(12) United States Patent
Shriver

(10) Patent No.: US 7,959,644 B2
(45) Date of Patent: Jun. 14, 2011

(54) HEMOSTATIC GUIDING CATHETER

(76) Inventor: Edgar L Shriver, Aventura, FL (US)

( * ) Notice: Subject to any disclaimer, the term of this patent is extended or adjusted under 35 U.S.C. 154(b) by 457 days.

(21) Appl. No.: 12/152,691

(22) Filed: May 16, 2008

(65) Prior Publication Data

US 2009/0287079 A1 Nov. 19, 2009

(51) Int. Cl.
*A61M 29/00* (2006.01)

(52) U.S. Cl. .................. 606/194; 604/96.01; 604/101.01

(58) Field of Classification Search .................. 606/191, 606/192, 194, 153; 604/96.01, 101.01, 103.05, 604/103.07, 528, 544, 910, 101.02–101.05, 604/103.08, 103.06, 93.01, 95.01–95.03, 604/97.01, 104, 915, 916; 623/1.11, 1.37; 600/435

See application file for complete search history.

(56) References Cited

U.S. PATENT DOCUMENTS

| | | | | |
|---|---|---|---|---|
| 2,849,002 A * | 8/1958 | Oddo | ........................... | 606/192 |
| 5,312,344 A * | 5/1994 | Grinfeld et al. | .......... | 604/101.05 |
| 5,486,195 A * | 1/1996 | Myers et al. | .................. | 606/213 |
| 5,916,194 A * | 6/1999 | Jacobsen et al. | ........... | 604/96.01 |
| 6,645,193 B2 * | 11/2003 | Mangosong | .................. | 604/506 |
| 6,743,208 B1 * | 6/2004 | Coyle | ........................ | 604/164.13 |
| 6,960,222 B2 * | 11/2005 | Vo et al. | ......................... | 606/200 |
| 7,306,575 B2 * | 12/2007 | Barbut et al. | ............... | 604/96.01 |
| 2003/0023204 A1 * | 1/2003 | Vo et al. | .................... | 604/103.07 |
| 2003/0195457 A1 | 10/2003 | LaFontaine et al. | | |
| 2004/0073238 A1 | 4/2004 | Makower | | |
| 2004/0116946 A1 * | 6/2004 | Goldsteen et al. | ............ | 606/153 |
| 2006/0089588 A1 * | 4/2006 | Scheule | ...................... | 604/6.16 |
| 2006/0111733 A1 | 5/2006 | Shriver | | |

* cited by examiner

*Primary Examiner* — Gary Jackson
*Assistant Examiner* — Katrina Stransky

(57) ABSTRACT

A hemostatic guiding catheter is biased to curve toward the artery wall and the distal opening is shaped so its edge is congruent with the artery wall. One or more annular balloons are inflated to produce a barrier between the guiding/catheter and the artery wall stopping the flow of blood and thus hemostasis. The annular balloons may be biased to inflate more on the side away from the distal opening thus imparting a force vector toward the distal opening and/or biased to overhang their line of attachment like a foreskin over a penis to allow the hemostatic guiding catheter to move a short distance while the biased balloons maintain hemostasis.

4 Claims, 2 Drawing Sheets

HEMOSTATIC GUIDING CATHETER

FEDERALLY SPONSORED RESEARCH

No

CROSS-REFERENCE TO RELATED APPLICATIONS

An invention by the same inventor disclosed in USPTO Pub. No.: 0111733, published by USPTO May 25, 2006, with substitute specification, claims and drawings submitted Jul. 15, 2006, includes a guiding/clamping catheter for achieving hemostasis. There are differences in coronary and peripheral artery situations that prevent one or more elements of the referenced previous invention from producing hemostasis in peripheral artery applications. Therefore, while having some similarity in appearance and objects with elements of the prior invention by the same inventor, the means described and claimed in the present invention for achieving the object of hemostasis in peripheral artery applications are considered to be independent of and not stepping on any elements of said prior invention.

FEDERALLY SPONSORED RESEARCH

Not Applicable

SEQUENCE LISTING OR PROGRAM

Not Applicable

BACKGROUND OF THE INVENTION

1. Field of the Invention

The field of the invention generally relates to catheters and balloons, specifically for percutaneously producing hemostasis in peripheral arteries 2. Prior Art Prior Art References:

| Pub. No. | Date | 1st author name |
|---|---|---|
| 0195457 | October 2003 | LaFontaine, et al |
| 0073238 | April 2004 | Makower |
| 0116946 | June 2004 | Goldsteen, et al |
| 0111733 | May 2006 | Shriver |

Methods for Restoring Blood Flow in Arteries

Revascularization restores blood flow in arteries by either going around or going through the occlusion restricting the flow. A bypass graft is the means of taking a supply of blood proximal to the occlusion site and going around the occlusion to deliver the blood to a site distal to the occlusion. At the present time surgery is the only approved method for placing a bypass graft. Percutaneous methods of revascularization go through rather than around the occlusion. Percutaneous entry is accomplished by a standard procedure of puncturing the skin with a hollow needle where the artery is large and close to the skin, commonly the femoral artery in the groin. A guiding catheter is inserted at the entry site and advanced toward coronary arteries or peripheral arteries, whichever are occluded. A common method of opening an occlusion is advancing a balloon on a catheter through the guiding catheter and into the occlusion where the balloon is inflated. This pushes open the occluded section of the artery and the balloon is deflated and removed. A newer method is to place a bare or drug eluting stent around the balloon to keep the occluded area propped open after the balloon is removed. Another option is advancing any one of many devices for removing occlusions through the guiding catheter to the site of occlusion. There are mechanical, electrical, chemical and cryogenic means of removal, chosen for the nature of the occlusion, e.g. calcified or thrombus-filled.

Most Effective Method

Of all the available revascularization methods the bypass graft is known to be most effective. But since surgery is presently the only procedure for placing bypass grafts, the less effective percutaneous methods are preferred since they involve almost none of the trauma, pain, risk, and long recovery time of surgery. The surgical trauma is not from connecting the ends of the bypass graft to the artery with tiny sutures in small arteriotomies. That is minor surgery though it requires high skill to place a suture a minute. The trauma is from gaining access to the arteries surgically, producing hemostasis, and harvesting a vein to use as the bypass graft. To gain access to coronary arteries the chest must be cleaved in two and ribs pulled back to expose the heart. The bypass graft is connected to the aorta as the source of blood for delivery through the bypass graft around the occlusion to the coronary artery distal to the occlusion. The aorta is usually clamped shut to achieve hemostasis. And since all the oxygenated blood from the heart is delivered through the aorta, it can't be clamped shut until the heart is stopped and a mechanical heart substituted to oxygenate and pump the blood to the body. Surgeons must work fast to finish suturing two or three bypass grafts in place within an hour, because risk goes up for longer time on the mechanical pump. Gaining access to peripheral arteries produces even higher mortality and morbidity than does gaining access to coronary arteries. Generally the surgical bypass patient is in intensive care for a day, a week in hospital and has many months of painful recovery. The patient treated by a percutaneous method is likely to be home in a day or so with essentially no pain. With this major difference in the effects of percutaneous and surgical treatment, it is not surprising that the less effective percutaneous treatments are selected about four times as often as the more effective bypass grafts.

Placing Bypass Grafts Percutaneously

It has long been obvious that if access for placing bypass grafts could be percutaneous, the graft's long-term effectiveness could be obtained without the undesirable surgical trauma. There have been four inventions published by the USPTO for devices to place bypass grafts percutaneously. Since coronary artery disease is the number one killer it is not surprising that all four use coronary arteries for their preferred embodiment. None specifically addresses unique conditions in peripheral arteries but each generally claims application to all vessels of the body. The devices described in these four inventions share certain objects that are common to all methods of placing bypass grafts. Two of these objects are making arteriotomies and achieving hemostasis. But the means of accomplishing these objects in a coronary situation are not applicable to peripheral artery situations because of critical differences in the two situations. One difference is that coronary arteries are in a fluid medium and the peripheral arteries in a tissue medium. A second difference is that the aorta at the coronary site is more than four times the diameter of a peripheral artery. A third difference is that blood in the aorta cannot be stopped without stopping the heart but this is not the case with a peripheral artery. Because of these differences the means provided in the previous inventions for achieving the objects of hemostasis and arteriotomies in a coronary application will not achieve those same objects in a peripheral artery application and/or are not needed in a peripheral artery situation. None of the four inventions has been shown to achieve the objects in the coronary situation for which they were designed as none have received the required US Federal Drug Agency approval for their use. No literature has been found that describes any attempts to apply them in peripheral arteries. The devices are discussed here in terms of whether the means they describe for achieving hemostasis are relevant as prior art to the means used by the present invention.

Mackower device In the invention by Mackower, the coronary vein is utilized as the bypass graft. The coronary vein runs parallel to the coronary artery and only a few millimeters from it on the surface of the heart within the liquid-filled pericardium. This short distance, with pericardial fluid between the vein and artery, and no involvement of the aorta, makes it possible for the Mackower device to use a sharp, short hollow tube to pierce the artery and enter the vein. This achieves hemostasis because the walls of both artery and vein are distended to allow the tube to pass while pressing tightly around the tube. The aorta is not the source of blood so the heart does not need to be stopped. A flexible seal is then pushed through the tube and allowed to expand in the lumen of the vein. The seal acts like an opened umbrella in the vein to prevent blood from escaping through the venous arteriotomy when the tube is withdrawn from the vein. The hollow tube is withdrawn into the artery where the other end of the seal is released. Thus the vein and artery are drawn toward each other in a side-to-side anastomosis. The vein and artery are connected on the other side of the occlusion in the same way. Incisions are then made in the chest to tie off the vein on either side of the two connections thus ending its function as a vein and making it a bypass graft. It may be noted that the vein is not turned around in this procedure. When sapheneous veins are used as coronary bypass grafts, they are turned around so the blood flows in the same direction it flowed when they were veins. It is reported in the literature that the coronary vein failed as a bypass graft. This may be because the vein was not turned around or because the coronary vein is too small to function as an artery or both, or for some other reasons not described. Whatever the reason, there are no means involved in the present invention that have any relationship to the means used in the Mackower device. The similarity is entirely in terms of objects, not prior art means.

LaFontaine device In the invention by La Fontaine, et al., hemostasis is achieved by an isolation device that applies a vacuum to the site of an arteriotomy. The patent application says this is to remove "blood from the region of the wall of the aorta where the incision is to be made and preclude additional blood flow from entering that area. Thus, a clear working space is created adjacent to the wall of the aorta . . . such that an incision can be made without a significant amount of blood being released from the aorta . . . through the incision." Whether or not this works in a coronary situation is not known. No report has been found in the literature of it being tried in a coronary or a peripheral artery situation. But the means described in the present invention for achieving hemostasis does not require a vacuum, but is accomplished by inflating one or more balloons in the peripheral artery to stop the flow of blood and thus create hemostasis. The present invention has one embodiment where the hemostatic guiding catheter carries a vacuum after hemostasis is achieved. A vacuum is used in medicine for many objects and in this case it is to pull tissue toward a cutting edge to accomplish an arteriotomy. There is no prior art described in the La Fontaine invention to compare with the art in the present invention.

Goldsteen device The invention by Goldsteen, et al., creates local hemostasis in the aorta around an arteriotomy as the opening is made. An arteriotomy is started with a stylet wire that makes an initial opening in the aorta. The means of increasing this tiny opening to the size needed for connecting to a bypass graft is described as using successively larger diameter sheaths to twist through the initial small opening. The assumption is that the aorta wall will remain in such close contact with the sheaths that no blood will escape around them. The sheaths are delivered through a guiding catheter that must be held against the aorta wall at a 90 degree angle. After an arteriotomy of the size needed is achieved, the guiding catheter is advanced through the opening. An annular balloon around the distal end of the guiding catheter is then inflated on the adventitial side of the aorta. This balloon presses against an annular balloon inside the aorta to squeeze the edge of the opening in the aorta between them. The Goldsteen patent application says the close spacing and resilient bias of the balloons toward each other helps to anchor the catheter to the aorta—and create hemostasis. It is not known if the Goldsteen device accomplishes the object of hemostasis in the aorta as there are no reports of trials in the literature. But it is known that the Goldsteen device entered trials several years ago but has not been approved for use by the US Food and Drug Agency. It is clear that the Goldsteen device requires the fluid medium surrounding the coronary aorta in which to open a balloon on the adventitial side of the aorta. Even if an arteriotomy could be accomplished in a peripheral artery by the Goldsteen device, the peripheral artery is surrounded by tissue and no means is provided in the Goldsteen device for entering this tissue or removing it in order to open a balloon. Also, since the Goldsteen device offers no other means of moving the catheter it has to be assumed it is moved by an operator pushing on the proximal end. This is routinely done with a catheter in the aorta to advance balloons and stents to occlusion sites. This is not a problem in the aorta which is about 36 mm in diameter and the guiding catheter is about 4 mm. This is a sufficient distance to turn the distal end of the guiding catheter 90 degrees from its longitudinal axis. The shape of the guiding catheter typically used to do this is that of a hockey stick. This places the distal end of the catheter at 90 degrees with respect to the aorta wall. It is not possible to make a 90 degree turn in a peripheral artery of 6-9 mm in diameter with a catheter of 4-7 mm in diameter. Thus sheaths cannot be delivered for twisting through the peripheral artery wall at an angle of 90 degrees with respect to the wall, as the Goldsteen device requires. The present invention provides the distal opening in the side of the catheter wall at an angle of 90 degrees to the longitudinal axis of the catheter and also provides balloons that apply force vectors to push the hemostatic guiding catheter toward the wall or through an opening in the wall. The present invention creates hemostasis by creating a barrier to the flow of blood in a peripheral artery by inflating one or more annular balloons around the guiding catheter inside the artery lumen. The present provides the means of placing a balloon on the adventitial side but after hemostasis is established. The means described in the Goldsteen device for hemostasis are not needed in the peripheral artery and cannot be applied because the artery is too small in circumference and the Goldsteen device provides no means of removing tissue surrounding the peripheral artery in order to open a balloon. Thus the Goldsteen device provides no prior art for comparison to the means used by the present invention for use in a peripheral artery application.

Shriver device The invention by Shriver uses a guiding catheter with two annular balloons on the distal end for use in coronary applications. The guiding catheter also has a double wall with one divider to provide two conduits for inflation fluid for the annular balloons. The catheter shape is described as being like those for balloon angioplasty such as "hockey stick" for turning the catheter across the aorta at a 90 degree angle and lodge against the side opposite the point of turn. The balloon and guiding catheter must be at a 90 degree angle to be effective. The catheter is placed at 90 degrees to the aorta wall and the proximal balloon is inflated before the opening is made in the aorta wall. This approach to the artery wall cannot be achieved in a peripheral artery because the peripheral artery is not large enough for the catheter to be turned 90 degrees. A cutting device is then lodged in the guiding catheter and the guiding catheter pushes the cutting device through the aorta wall. The assumption is that blood will not escape around the guiding/clamping catheter before an annular balloon can be inflated on the adventitial side of the aorta to clamp the artery wall between that balloon and a balloon inflated in the lumen of the artery. Even if that assumption is true the prior art cutting element has only the force vector in line with the longitudinal axis of the aorta to push against the aorta wall at a 90 degree angle and that is not possible in the peripheral artery situation. And no means are provided in the Shriver device for removing tissue on the adventitial side of the artery in order to open a balloon. Thus, the elements of the prior art Shriver device for making an arteriotomy and achieving hemostasis in the fluid environment and large aorta of a coronary application cannot achieve the same objects in a peripheral artery situation so they are not prior art with respect to the present invention. There are two inflation fluid conduits described in the prior Shriver device that are modified in one embodiment of the present invention to provide a larger number of conduits. Whether or not this is an obvious difference with respect to the prior art is not known. But it is clear that the Shriver device does not provide prior art for achieving hemostasis in peripheral arteries.

3. Objects and Advantages

The object is to produce hemostasis at a pre-selected site in a peripheral artery by percutaneous means that also provide a closed pathway for guiding other devices to the artery wall at this site. The advantages over prior art are:

1. Providing a hemostatic guiding catheter slightly smaller than the diameter of the artery in which it is used that bends at an angle from the longitudinal axis toward the artery wall thus stopping the flow of blood through most of the artery area and deflecting any longitudinal element being guided through the hemostatic guiding catheter toward the artery wall.

2. Providing a hemostatic guiding catheter with a distal opening in the shape produced by intersecting the bent distal end with a cylinder the circumference of the artery in which the hemostatic guiding catheter is intended for use, thus creating a distal opening with edge contiguous with the artery wall.

3. Providing a hemostatic guiding catheter with one or more annular balloons near the distal end that inflate to produce a barrier between the hemostatic guiding catheter and the artery wall to obstruct the flow of blood in the artery, thus creating hemostasis.

4. Providing a hemostatic guiding catheter with a smooth, continuous, hard, inner surface that will smoothly deflect longitudinal elements such as a steerable piercing guidewire, an anchor wire, a delivery catheter, and excision/incision cup, and also provide a suitable conduit for a vacuum applied at the proximal end to the distal opening.

5. Providing one or more annular balloons near the distal end of the hemostatic guiding catheter for additional purchase on the artery wall thus preventing slippage of the hemostatic guiding catheter and distributing the pressure on the artery so the pressure is not concentrated on an artery with reduced elasticity.

6. Providing a hemostatic guiding catheter with one or more annular balloons that are biased to inflate more on the side away from the distal opening than on the side of the distal opening to provide lateral movement of the guiding catheter in an artery and to push the hemostatic guiding catheter tightly against the distal opening.

7. Providing a hemostatic guiding catheter with annular balloons shaped to extend from their line of attachment over the guiding catheter to which they are attached, like a foreskin over a penis enabling adjacent annular balloons to push against each other to increase the pressure produced by each and to enable the balloons to roll back as the catheter moves forward. This allows a short forward motion as through an arteriotomy or a forward-and-back sawing motion while the foreskin shaped balloon(s) maintain(s) hemostasis through contact with the wall of the artery. Either of these effects can be useful in connection with other elements of percutaneous devices for placing bypass grafts.

SUMMARY OF THE INVENTION

A hemostatic guiding catheter of somewhat smaller circumference than the peripheral artery, into which it is percutaneously introduced, is advanced to a site proximal to an occlusion. The distal end of the hemostatic guiding catheter is manufactured to curve toward the artery wall. The distal opening is cut so its edge is contiguous with the wall of the artery. One or more annular balloons, attached around the distal end is/are inflated to produce a barrier in the space between the hemostatic guiding catheter and the wall of the artery. Annular balloons may also be shaped to inflate with one or more biases. One bias causes an annular balloon to inflate more on the side away from the distal opening which pushes the edge of the distal opening in the hemostatic guiding catheter firmly against the artery wall. Another bias causes the annular balloon to overhang its line of attachment so it inflates over the hemostatic guiding catheter like a foreskin over a penis. This allows adjacent annular balloons to abut and push against each other increasing the pressure that can be achieved over that obtained by one balloon against the artery wall. This also allows a small movement of the hemostatic guiding catheter in the annular balloon while the balloon maintains the hemostatic barrier. Channels are provided for fluid inflation of each balloon. In an alternate embodiment, one or more channels are provided to carry contrast fluid distal to the barrier of inflated annular balloons to port into the peripheral artery. This porting of contrast fluid and the means of movement are provided to contribute to the operation of other percutaneous elements that use the hemostatic guiding catheter to guide them to the performance of their function in placing a bypass graft, e.g. excision/incision arteriotomy cup, steerable, piercing guidewire, graft delivery catheter, holding balloons, etc.

| Key |
|---|
| 1. surrounding tissue |
| 2. peripheral artery |
| 3. artery wall |
| 4. occlusion |
| 5. hemostatic guiding catheter |
| 6. distal opening |
| 7. fluid supply lines |
| 8. most distal annular balloon |
| 9. dividers |
| 10. next most distal annular balloon |
| 11. fluid channels |
| 12. least distal annular balloon |
| 13. contrast fluid port |

DETAILED DESCRIPTION OF THE PREFERRED EMBODIMENTS

Having thus described the figures, methods and means in accordance with the present invention are now described with reference thereto. It should be understood that steps described for each process may be omitted or the order changed or performed simultaneously without deviating from the spirit or scope of the invention. It should be understood that a specific application situation involving a peripheral artery with an occlusion is used to represent the general case of a vessel in a mammalian body. Further, it should be recognized that other devices are used with the hemostatic guiding catheter described here. An example is a steerable, piercing, anchoring guidewire device that makes an opening in an artery wall by piercing then dilating the opening. Another example is a delivery catheter for delivering a bypass graft.

The following description of preferred embodiments should be read with reference to the drawings, in which the elements in different drawings are numbered in like fashion. The drawings, which are not necessarily to scale, depict selected embodiments and are not intended to limit the scope of the invention. Examples of construction, dimensions, materials, and manufacturing processes are provided for various elements but merely as a reflection of current manufacturing practice. Those skilled in the art will recognize that many of the examples provided have suitable alternatives which may be utilized now and in the future.

Figure 1A:
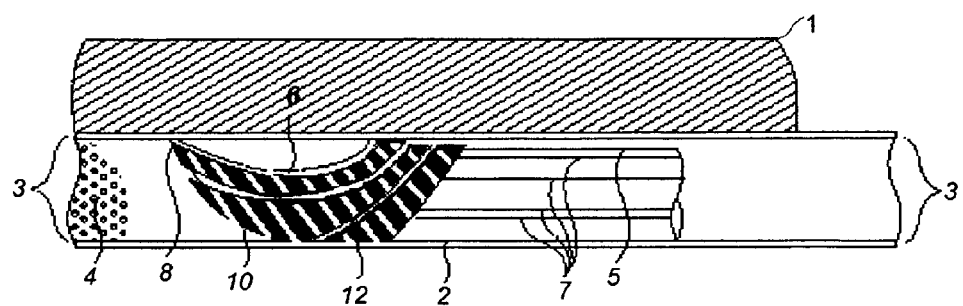
FIG. 1A is a cross section view of a hemostatic guiding catheter and three uninflated annular balloons with fluid supply lines in the lumen of a peripheral artery with an occlusion and surrounded by tissue.

FIG. 1A shows artery 2 and surrounding tissue 1, represented in a cross-sectional view by hatched lines. Surrounding tissue 1 may be aponeurotic, fatty, muscle or other types and may contain other processes such as nerves and veins that must not be injured. To provide the physician with the device configurations and methods for dealing with these and other situations, several embodiments of the invention are provided. This figure shows a cross sectional view of hemostatic guiding catheter 5 advanced in peripheral artery 2 to a point proximal to occlusion 4 that is to be bypassed with a graft. Hemostasis is produced before the arteriotomy is made so blood will not pour out of artery 2 before the bypass graft is connected. The distal end of hemostatic guiding catheter 5 turns away from its longitudinal axis at an angle. Distal opening 6 is produced during manufacture as the intersection of hemostatic guiding catheter 5 with a cylinder of the same circumference as the lumen of the artery in which the hemostatic guiding catheter is to be used. This causes distal opening 6 to be saddle-shaped, facing at 90 degrees with respect to the longitudinal axis of hemostatic guiding catheter 5, and having an edge that is congruent and contiguous with artery wall 3 at all points on its circumference. Hemostatic guiding catheter 5 is constructed of a material such as stainless steel, NITINOL, polyester, or other hard semi-flexible material such as in a hypotube made by Creganna. The material should create a smooth, hard, non-porous interior wall that will deflect longitudinal elements it guides and carry a vacuum applied at the proximal end to distal opening 6 and thus to the portion of artery wall 3 stretching across distal opening 6. Three annular balloons are shown in the uninflated state on their lines of attachment toward the distal end of guiding catheter 5. Three annular balloons are used here to represent one or more annular balloons. For convenience, these annular balloons are referred to as most distal balloon 8, next most distal balloon 10, and least distal balloon 12, without implying the existence of any number of balloons other than one or more. The one or more annular balloons are made of such materials as polyurethane, nylon elastomers or other thermoplastic elastomers and attached around hemostatic guiding catheter 5. Their lines of attachment are generally at right angles with respect to the curvature where they are attached. Inflating most distal balloon 8 produces a barrier between the edge of distal open end 6 and artery wall 3, thus tending to produce hemostasis around distal opening 6 but without stopping the flow of blood elsewhere around the circumference of hemostatic guiding catheter 5. Inflating next most distal balloon 10 creates a barrier between hemostatic guiding catheter 5 and artery wall 3 thus tending to stop the flow of blood in artery 2, and thus producing hemostasis distal to the inflated next most distal balloon 10. Distal opening 6 is shown to be distal to this barrier produced by inflating next most distal balloon 10. Inflating least most distal balloon 12 and any additional annular balloons has the same barrier effect as inflating next most distal balloon 10. But the more annular balloons inflated the larger the surface area of contact between the balloons and artery wall 3 thus increasing the purchase of hemostatic guiding catheter 5 on artery wall 3 to prevent slippage and also to reduce the pressure needed by any one of one or more annular balloons to produce hemostasis. In alternative embodiments one or more annular balloons are manufactured with a bias. One bias is making the balloon inflate more on the side opposite distal opening 6 than on the side of distal opening 6. Thus when inflated the bias produces a force vector that pushes hemostatic guiding catheter 5 toward distal opening 6. This tends to ensure a tight fit between the edge of distal opening 6 and artery 2 where they are in contiguous contact, thus tending to ensure hemostasis around distal opening 6. If there is an opening in artery wall 3 within the circumference of distal opening 6 the force vector from the biased annular balloons of this embodiment can push hemostatic guiding catheter 5 through that opening. One or more annular balloons have one or more fluid supply lines 7 in these two embodiments. In another embodiment one or more additional fluid supply lines are added for carrying contrast fluid and/or saline solution distal to the hemostatic barrier. To illustrate this embodiment, four fluid supply lines 7 are shown attached longitudinally to the outside of the hemostatic guiding catheter 5. That is one more than needed to supply the three annular balloons used here to represent one or more annular balloons. This is the embodiment used when an extravascular steerable guidewire is used with hemostatic guiding catheter 5 to dilate an arteriotomy and pierce a pathway for placement of a bypass graft. The guidewire device requires that contrast fluid be in artery 2 distal to the site of hemostasis to make artery 2 visible on a fluro-unit. This is different from the embodiment used when the guidewire device is not used to produce an arteriotomy. The embodiment for use with some other device than the guidewire for producing an arteriotomy requires only one fluid supply line for each of one or more annular balloons—or three fluid supply lines for the three annular balloons used here to represent one or more annular balloons. In both embodiments fluid supply lines 7 are attached in such a way that they do not produce a source of leakage where one or more supply lines goes under an annular balloon at some point along its line of attachment to hemostatic guiding catheter 5.

Figure 1B:
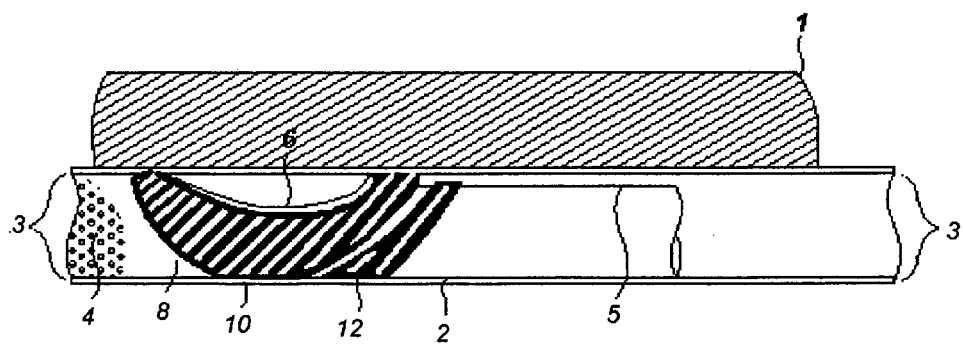
FIG. 1B shows the same elements as FIG. 1A with one annular balloon inflated to show how it blocks the flow of blood in the artery and thus achieves hemostasis.

FIG. 1B shows next most distal annular balloon 10 inflated to demonstrate another alternative embodiment in which a type of bias is used that causes said one or more annular balloons to inflate with an overhang away from their line of attachment to hemostatic guiding catheter 5 like a foreskin over a penis. Thus next most distal balloon 10 is shown moving away from its line of attachment (as was shown in FIG. 1A) over hemostatic guiding catheter 5. Most distal balloon 8 is not seen. This illustrates three possible reasons. First, because the distally biased next most distal balloon 10 covers most distal balloon 8 when inflated. Second, if most distal balloon 8 is inflated before next most distal balloon 10 the two balloons abut, creating the same appearance but producing more pressure against artery wall 3 around the edge of distal opening 6 than the pressure produced by next most distal balloon 10 alone or most distal balloon 8 alone. And third, most distal balloon 8 may not be utilized in this particular embodiment. With the foreskin bias, next most distal balloon 10 creates a barrier to the flow of fluid in artery 2 when inflated just as it does with no bias or with a bias to inflate toward distal opening 6. The objects of the inflated foreskin shape are to abut and increase pressure, and to allow a small movement of hemostatic guiding catheter 5 in the distal-proximal direction while hemostasis is maintained and to allow the edge of an arteriotomy in artery wall 3 to be clamped between most distal balloon 8 and next most distal balloon 10. Least distal balloon 12 and any balloons in addition to the representative three shown here are located proximally to least distal balloon 12 and generally shaped like least distal annular balloon 12. When inflated they further increase purchase against wall 3 and reduce the pressure required on a particular segment of artery to achieve hemostasis. The physician may choose a hemostatic guiding catheter 5 with more balloons when the patient has arteries that have lost most of their original elasticity. The physician also chooses other devices to be guided through hemostatic guiding catheter 5 to perform additional functions for placing a bypass graft. And the physician also chooses the embodiment of the hemostatic guiding catheter device that best supports the additional devices chosen.

Figure 1C:
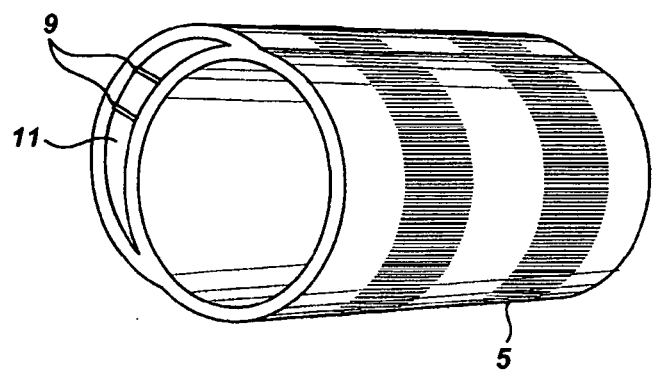
FIG. 1C shows two annular balloons on a cross section of a catheter that has a double wall with two dividers creating three conduits for delivering inflation fluid.

FIG. 1C shows a cross section of hemostatic guiding catheter 5 that has a double wall. The double wall creates a crescent-shaped lumen. Two dividers 9 are shown that create three conduits that can serve as supply lines 7 for delivering fluid to one or more annular balloons. This embodiment is similar to an embodiment in a prior invention by the same inventor that has been previously discussed and referenced, but that invention includes only one divider and two conduits in the crescent-shaped lumen created by a double wall. The addition of a second divider in this figure represents two or more dividers 9 producing three or more conduits. This is a variation from the prior art invention to serve the requirements of the present invention for more dividers and conduits than provided in the prior art. The present invention includes one or more annular balloons. This number may be more or less than two annular balloons described and shown in the prior art. The present invention has one embodiment where fluid supply lines 7 provide inflation fluid to each of one or more annular balloons and an embodiment in which an additional one or more of fluid supply lines 7 provides contrast fluid in artery 2 distal to one or more annular balloons. The present invention does not claim what is claimed in the prior art, but it claims the variations that are represented here by two or more dividers 9. The advantages of a double wall with dividers 9 creating conduits is that it requires less space than individual walls on each supply line and makes leakage less likely.

Figure 1D:
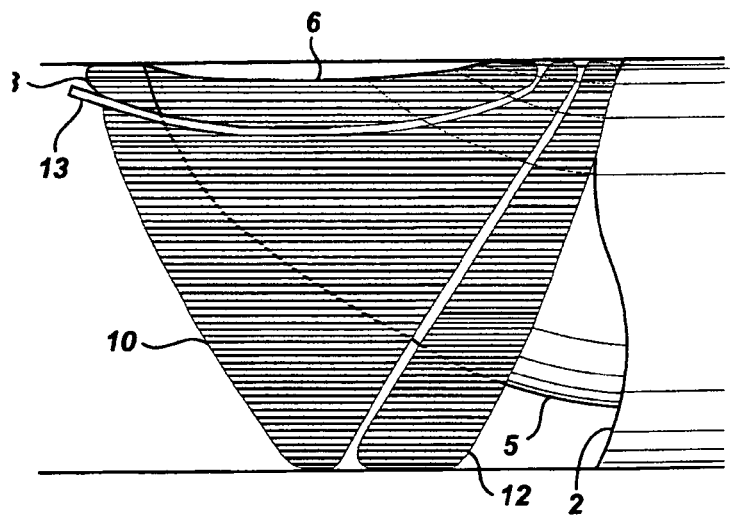
FIG. 1D shows three annular balloons inflated on a hemostatic guiding catheter with a port for contrast/saline fluid located between two abutting balloons so as to carry fluid to the artery distal to the inflated annular balloons.

FIG. 1D shows hemostatic guiding catheter 5, and annular balloons 8, 10, and 12 inflated inside artery 2, with part of the side of artery 2 removed to show what is inside. This figure is used to show the alternative embodiments where balloons are biased and contrast fluid is delivered distal to the inflated balloons. This embodiment also includes fluid port 13 shown between most distal balloon 8 and next most distal balloon 10. This port is located between annular balloons so no balloon has to be pierced to allow the contrast fluid port 13 to pass through it to deliver contrast fluid distal to the hemostatic barriers of inflated next most distal balloon 10 and least distal balloon 12. The embodiment with contrast fluid is selected when the physician chooses to use the hemostatic guiding catheter to guide a device that requires contrast fluid in artery 2 to accomplish its object in placing a bypass graft. A white line is shown between balloons though in reality they will abut with no space between them. The hemostatic guiding catheter 5 is shown as being in the lumen of artery 2, but it can be seen that the biased next most distal balloons 10 and least most distal balloon 12 can produce a force vector that, combined with the force vector from pushing the distal end of hemostatic guiding catheter 5, will push hemostatic guiding catheter 5 through any opening that is made in artery 2 within the circumference of distal opening 6.

What is claimed is:

1. A hemostatic guiding catheter device for establishing a tubular passageway in a peripheral artery or vein from entry at a percutaneous site through an arteriotomy site to a site distal to said entry and for preventing blood from flowing out of said arteriotomy site, said hemostatic guiding catheter having an outside circumference and an inside circumference with a wall therebetween, a proximal end, a distal end, and a lumen therebetween, said lumen having a proximal opening and a distal opening; said hemostatic guiding catheter being smaller in said outside circumference than the inside circumference of said peripheral artery or vein; and being made of a hard, semi-flexible material such as wound stainless steel wire, flexible metal or polymers;

said hemostatic guiding catheter having a permanently bent shape for pointing said distal opening away from said longitudinal axis and toward said arteriotomy site and deflecting elongated instruments or other objects guided inside said lumen;

said distal opening having a saddle-shaped edge congruent with a shape of the arteriotomy site on said peripheral artery or vein;

one or more annular balloons attached to said distal end of said hemostatic guiding catheter, the one or more annular balloons having a pre-selected shape when inflated that constitute one or more barriers to the flow of blood and made of such material as polyurethane or thermoplastic elastomers;

one of said one or more annular balloons, always present and nominally called next most distal balloon, biased to inflate with an extreme overhang away from a point of attachment around said edge of the distal opening, like a foreskin over a penis, thus forming a tube shape ending in a saddle-shaped edge at a junction with said artery wall to constitute a first second barrier to the flow of blood into said arteriotomy, and expanding largely in the direction opposite to said arteriotomy site to push against said artery wall opposite said arteriotomy site and also in all directions to fill a space between said outside circumference of said hemostatic guiding catheter and said inside circumference of said peripheral artery to constitute a second barrier to the flow of blood, wherein at least a portion of said hemostatic guiding catheter located inside said next most distal balloon slides forward like a penis through said arteriotomy; and one or more flexible tubes for carrying fluid from outside said percutaneous opening to said one or more annular balloons, said flexible tubes being made of a polymeric material, wherein said hemostatic guiding catheter provides a tubular passageway for guiding elongated instruments and other objects through and out of said peripheral artery to form the arteriotomy and a bypass graft around an occlusion in said peripheral artery.

2. The device of claim 1 wherein another of said one or more balloons, nominally called most distal balloon is attached around said distal end of said hemostatic guiding catheter, and having an uninflated state, that is sufficiently flat so as not to prevent passage through said arteriotomy or prevent said next most distal balloon from extending over it; and an inflated state having a saddle-shape adapted to constitute a third barrier to the flow of blood into said arteriotomy made within said distal opening; and wherein said most distal balloon inflates on said adventitial side of said peripheral artery to provide the means for squeezing the edge of said arteriotomy against said next most distal balloon.

3. The device of claim 1 wherein another of said one or more balloons, nominally called least distal balloon is attached around said hemostatic guiding catheter proximal to said next most distal balloon, the least distal balloon having an uninflated state and an inflated state, wherein said least distal balloon when in an inflated state fills the space between said outside circumference of said hemostatic guiding catheter and said wall of said peripheral artery forming a fourth barrier to the flow of blood in said peripheral artery distal to said least distal balloon and prevents the movement of said hemostatic guiding catheter in said peripheral artery.

4. The device of claim 1 wherein said wall of said hemostatic guiding catheter is double on one side to create a crescent-shaped lumen extending from said distal end to said proximal end, the crescent-shaped lumen having one or more divisions forming two or more channels in said crescent-shaped lumen, and one of said two or more channels opening to said one of said one or more balloons and the other of the one or more channels opening to a short length of flexible tubing extending distal to said one or more balloons where said short length of flexible tubing ends in a fluid port.

* * * * *